(12) United States Patent
Doi et al.

(10) Patent No.: US 9,572,500 B2
(45) Date of Patent: Feb. 21, 2017

(54) ELECTRONIC SPHYGMOMANOMETER

(75) Inventors: Ryosuke Doi, Kyoto (JP); Takanori Nishioka, Nagaokakyo (JP); Kohei Takeoka, Kyoto (JP); Yukiya Sawanoi, Nara (JP); Kenichi Horibata, Kyoto (JP); Masataka Yanagase, Osaka (JP); Izumi Hachimaru, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 380 days.

(21) Appl. No.: 13/469,497

(22) Filed: May 11, 2012

(65) Prior Publication Data

US 2012/0226170 A1 Sep. 6, 2012

Related U.S. Application Data

(63) Continuation of application No. PCT/JP2010/069799, filed on Nov. 8, 2010.

(30) Foreign Application Priority Data

Nov. 13, 2009 (JP) ................................. 2009-259829

(51) Int. Cl.
*A61B 5/02* (2006.01)
*A61B 5/022* (2006.01)

(52) U.S. Cl.
CPC ........... *A61B 5/022* (2013.01); *A61B 5/02225* (2013.01)

(58) Field of Classification Search
USPC ................................................ 600/480–515
See application file for complete search history.

(56) References Cited

U.S. PATENT DOCUMENTS 3,090,377 A * 5/1963 Salisbury ........... A61B 5/02133
                                                   600/490
4,269,193 A * 5/1981 Eckerle .................. A61B 5/021
                                                   600/485
(Continued)

FOREIGN PATENT DOCUMENTS

JP      61-288833 A     12/1986
JP      02-019133 A      1/1990
(Continued)

OTHER PUBLICATIONS

Office Action issued Nov. 7, 2014 in corresponding Russian Application Na 2012124117114(036833) (with translation) (7 pages).
(Continued)

*Primary Examiner* — Michael Kahelin
*Assistant Examiner* — Mitchell E Alter
(74) *Attorney, Agent, or Firm* — Osha Liang LLP

(57) ABSTRACT

A first oscillation circuit and a second oscillation circuit are connected to a first pressure sensor and a second pressure sensor, respectively, and oscillate based on the capacity values of the corresponding pressure sensors. The first oscillation circuit and the second oscillation circuit operate in response to instruction from a CPU. The one of the first oscillation circuit and the second oscillation circuit that has received an activation signal from the CPU outputs a signal having a frequency that corresponds to the capacity value of the corresponding pressure sensor. An adjustment circuit is connected to the first oscillation circuit and the second oscillation circuit, and allows one of the frequency signals to pass therethrough, outputting the signal to the CPU.

5 Claims, 9 Drawing Sheets

(56) References Cited

U.S. PATENT DOCUMENTS

| | | | |
|---|---|---|---|
| 4,378,807 A * | 4/1983 | Peterson | A61B 5/02141 |
| | | | 128/900 |
| 4,493,326 A * | 1/1985 | Hill | A61B 5/02208 |
| | | | 600/493 |
| 4,953,557 A | 9/1990 | Frankenreiter et al. | |
| 4,971,063 A * | 11/1990 | Flachslaender et al. | 600/490 |
| 5,680,870 A * | 10/1997 | Hood et al. | 600/495 |
| 6,443,905 B1 * | 9/2002 | Nissila | A61B 5/0002 |
| | | | 600/490 |
| 7,594,892 B2 | 9/2009 | Cen et al. | |
| 2002/0169380 A1 * | 11/2002 | Hasegawa | A61B 5/021 |
| | | | 600/485 |
| 2006/0064023 A1 * | 3/2006 | Yang | A61B 5/022 |
| | | | 600/490 |
| 2009/0076345 A1 * | 3/2009 | Manicka | A61B 5/4875 |
| | | | 600/301 |
| 2010/0268300 A1 * | 10/2010 | Ramos Leal | A61N 1/326 |
| | | | 607/50 |
| 2011/0092830 A1 * | 4/2011 | Chen | A61B 5/0225 |
| | | | 600/490 |

FOREIGN PATENT DOCUMENTS

| | | | |
|---|---|---|---|
| JP | H02-1226 A | | 1/1990 |
| JP | 07-051233 A | | 2/1995 |
| WO | WO 2008/143487 | * | 11/2008 |
| WO | 2009/093515 A1 | | 7/2009 |
| WO | WO 2009/143780 | * | 12/2009 |
| WO | 2010026868 A1 | | 3/2010 |

OTHER PUBLICATIONS

Patent Abstracts of Japan, Publication No. 07-051233, publication date Feb. 28, 1995 (1 page).

Patent Abstracts of Japan, Publication No. 02-019133, publication date Jan. 23, 1990 (1 page).

International Search Report issued in PCT/JP2010/069799 mailed on Nov. 30, 2010, with English translation thereof, 3 pages.

* cited by examiner

ELECTRONIC SPHYGMOMANOMETER

TECHNICAL FIELD

This invention relates to electronic sphygmomanometers, and particularly relates to electronic sphygmomanometers that improve the reliability of blood pressure measurement values.

BACKGROUND ART

Blood pressure is one index for analyzing cardiovascular disease. Performing a risk analysis for cardiovascular disease based on blood pressure is effective in preventing cardiovascular-related conditions such as stroke, heart failure, and myocardial infarction. In particular, morning hypertension, in which the blood pressure rises in the early morning, is related to heart disease, stroke, and the like.

Furthermore, among morning hypertension symptoms, the symptom called "morning surge", in which the blood pressure rapidly rises within one hour to one and a half hours after waking up, has been found to have a causal relationship with stroke. Accordingly, understanding the interrelationship between time (lifestyle) and changes in blood pressure is useful in risk analysis for cardiovascular-related conditions. It is therefore necessary to continuously measure blood pressure over a long period of time.

Furthermore, recent study results have shown that home blood pressure, which is blood pressure measured at home, is more effective in the prevention, diagnosis, treatment, and so on of cardiovascular-related conditions than blood pressure measured at a hospital or during a health examination (casual blood pressure). Accordingly, sphygmomanometers for home use have become widely prevalent, and home blood pressure values have started to become used in diagnoses.

In order to improve the measurement precision of sphygmomanometers, JP H7-51233A discloses an invention in which processing for correcting error in a measurement value that is dependent on the characteristics of the pressure sensor for blood pressure measurement is performed in the electronic sphygmomanometer production stage.

JP H2-19133 and U.S. Pat. No. 7,594,892 disclose techniques for improving the reliability of blood pressure measurement values using two pressure sensors.

According to the electronic sphygmomanometer disclosed in Patent Literature 1, the correction regarding the pressure sensor is performed based on differences in the characteristics of the individual electronic sphygmomanometers during the electronic sphygmomanometer production stage. However, unlike a sphygmomanometer used in a medical facility such as a hospital, a sphygmomanometer for home use is generally not periodically corrected after purchase, except for in certain situations such as a malfunction.

For example, even if the pressure sensor output, which is of utmost importance in blood pressure measurement, deviates beyond a specified tolerance margin, there is no way to know that this has happened, and therefore, it is not clear whether blood pressure measurement values are correct. For this reason, even if there is a large difference between a blood pressure measurement value and the normal blood pressure measurement value or the casual blood pressure measurement value, it is not clear whether the blood pressure values are actually different, or the blood pressure values are different due to error in the pressure sensor of the sphygmomanometer, thus causing concern on the part of the user.

Meanwhile, some sphygmomanometers for medical facilities include two pressure sensors, and pressure is monitored based on the output of these pressure sensors. However, the functions of these two pressure sensors are used for different purposes in such sphygmomanometers. That is, the blood pressure is calculated using cuff pressure information obtained by one of the pressure sensors, and abnormality detection is performed based on the output of the other pressure sensor.

Specifically, an abnormality is detected if the pressure value detected by the pressure sensor greatly exceeds 300 mmHg, for example. In this case, safety is ensured by stopping the pump and releasing the valve. Accordingly, the other pressure sensor is applied as a safety measure specified in the medical standard IEC 60601-2-30, and does not guarantee the precision of the one pressure sensor used for blood pressure measurement.

In light of this, it is necessary for the precision of the one pressure sensor, which is used for detecting blood pressures, to be guaranteed by that pressure sensor itself. There is thus a demand for a high-precision pressure sensor that is not influenced by external disturbances such as temperature changes, that changes little over time, and that is inexpensive. Furthermore, providing two pressure sensors that perform different functions means that the malfunction rate of the sphygmomanometer due to malfunctions in the pressure sensors will simply be double the malfunction rate of a sphygmomanometer that has only one pressure sensor.

CITATION LIST

Patent Literature

Patent Literature 1: JP-H7-51233A
Patent Literature 2: JP-H2-19133A
Patent Literature 3: U.S. Pat. No. 7,594,892

SUMMARY OF INVENTION

Meanwhile, although using two or more pressure sensors in order to improve the measurement precision of an electronic sphygmomanometer, measuring pressures using the respective pressure sensors, and then comparing or averaging the results can be considered as one way to improve the precision, it is then necessary to provide the same number of analog input terminals, which function as sensor input terminals for a CPU (Central Processing Unit), as there are pressure sensors. Under this method, the scale of the circuit grows, and the same CPU as that employed in conventional electronic sphygmomanometers cannot be used.

A less expensive CPU that has only a single analog input terminal serving as a sensor input terminal requires a circuit for switching among the outputs from the multiple pressure sensors, which makes it necessary to employ a complex, high-cost relay circuit or analog switching circuit. It is also necessary to consider that such a circuit must have transmission properties such that the amplitude, frequency, and so on of the signal outputted from the pressure sensor are not altered.

Meanwhile, there is the chance that the signals outputted from multiple pressure sensors will interfere with each other electromagnetically in the circuit, causing erroneous operation, and thus, it is necessary to ensure that the circuit board has a sufficient degree of electromagnetic insulation in order to obtain an accurate measurement.

Furthermore, using multiple pressure sensors simultaneously leads to an increase in the amount of power consumed in proportion to the number of pressure sensors, which reduces the number of times the sphygmomanometer can be used, particularly in battery-operated products. CPUs that have a large circuit scale also consume more power.

Therefore, one or more embodiments of the present invention provide an electronic sphygmomanometer that can, using a simple system, improve the reliability of blood pressure values using multiple pressure sensors.

An electronic sphygmomanometer according to one or more embodiments of the present invention includes: a cuff that is worn on a measurement area; an inflation and deflation unit that adjusts a pressure applied to the cuff; a plurality of pressure sensors connected to the cuff; a plurality of oscillation circuits, provided in correspondence to the respective plurality of pressure sensors, that output a square wave signal of a frequency based on pressures; an oscillation circuit adjustment circuit, provided in common for the plurality of oscillation circuits, that allows the output from one of the plurality of oscillation circuits to pass; and a control circuit that accepts the input of the square wave signal from the oscillation circuit adjustment circuit and calculates a blood pressure from the frequency of the square wave signal.

According to one or more embodiments of the present invention, the oscillation circuit adjustment circuit includes a logic circuit, having a plurality of input nodes that accept inputs from the respective plurality of oscillation circuits, that outputs one signal based on the result of a logic process performed on the signals inputted into the plurality of input nodes.

According to one or more embodiments of the present invention, each of the oscillation circuits outputs a square wave signal of a frequency based on the pressure when the oscillation circuit has been activated in accordance with an instruction, and outputs a fixed voltage signal in the case where the oscillation circuit has not been activated.

According to one or more embodiments of the present invention, the control circuit switches the oscillation circuit that is active among the plurality of oscillation circuits by outputting an activation signal to the plurality of oscillation circuits.

According to one or more embodiments of the present invention, the control circuit outputs a first activation signal to a first oscillation circuit among the plurality of oscillation circuits and detects a first cuff pressure based on the frequency of a first square wave signal outputted from the first oscillation circuit. The control circuit outputs a second activation signal to a second oscillation circuit among the plurality of oscillation circuits and detects a second cuff pressure based on the frequency of a second square wave signal outputted from the second oscillation circuit. The control circuit determines whether or not an abnormality has occurred in the plurality of pressure sensors based on a difference between the first cuff pressure and the second cuff pressure.

According to one or more embodiments of the present invention, the control circuit outputs a third activation signal to the first oscillation circuit among the plurality of oscillation circuits after outputting the first activation signal and the second activation signal, and detects a third cuff pressure based on the frequency of the first square wave signal outputted from the first oscillation circuit; and the control circuit determines whether or not an abnormality has occurred in the plurality of pressure sensors based on a difference between an average of the first and third cuff pressures and the second cuff pressure.

According to one or more embodiments of the present invention, an oscillation circuit adjustment circuit allows one of the outputs from the plurality of oscillation circuits to pass, the control circuit accepts the input of the square wave signal from the oscillation circuit adjustment circuit, and the blood pressure is calculated based on the frequency of the square wave signal. Therefore, it is possible, using a simple system, to improve the reliability of blood pressure measurement values using a plurality of pressure sensors.

DETAILED DESCRIPTION OF INVENTION

Figure 1:
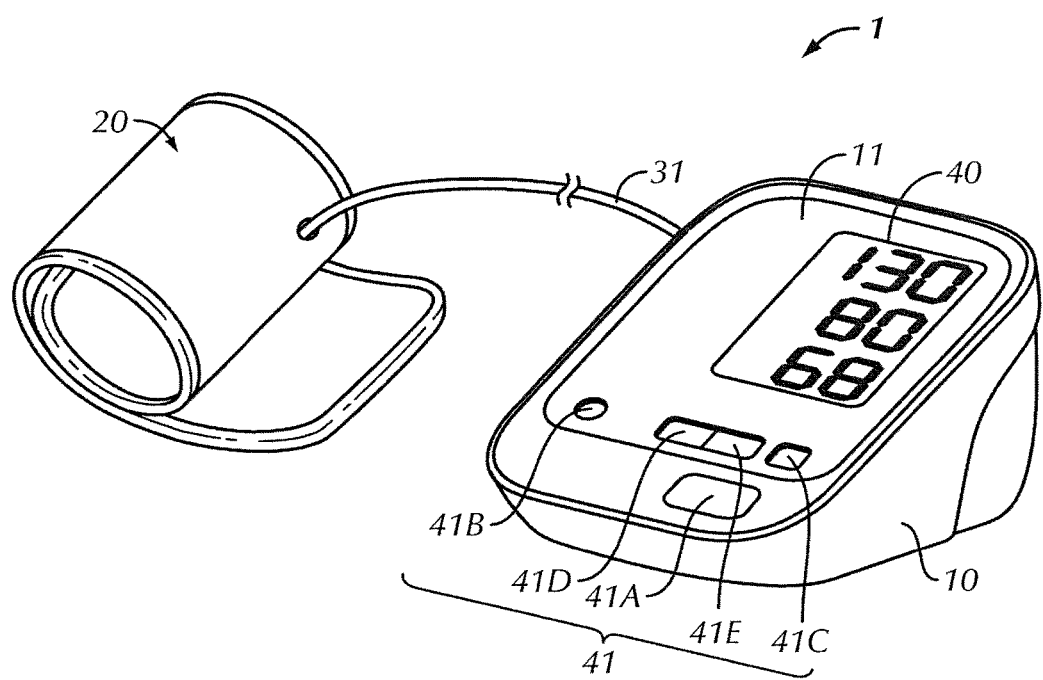
FIG. 1 is a diagram illustrating an external view of an electronic sphygmomanometer 1 according to an embodiment of the present invention.

Hereinafter, an electronic sphygmomanometer according to one or more embodiments of this invention will be described with reference to the drawings. When numbers, amounts, and so on are discussed in the following embodiments, it should be noted that unless explicitly mentioned otherwise, the scope of the present invention is not necessarily limited to those numbers, amounts, and so on.

Furthermore, in the case where multiple embodiments are described hereinafter, it is assumed from the outset that the configurations of the respective embodiments can be combined as appropriate unless explicitly mentioned otherwise. In the drawings, identical reference numerals refer to identical or corresponding elements. There are also cases where redundant descriptions are omitted.

The present embodiment describes an electronic sphygmomanometer that calculates blood pressures through an oscillometric method using the upper arm as a measurement area, and as an example, includes two pressure sensors. Note that the method applied for the blood pressure calculation is not limited to an oscillometric method.

External View of Electronic Sphygmomanometer 1

FIG. 1 is a diagram illustrating an external view of an electronic sphygmomanometer 1 according to an embodiment of the present invention.

Figure 2:
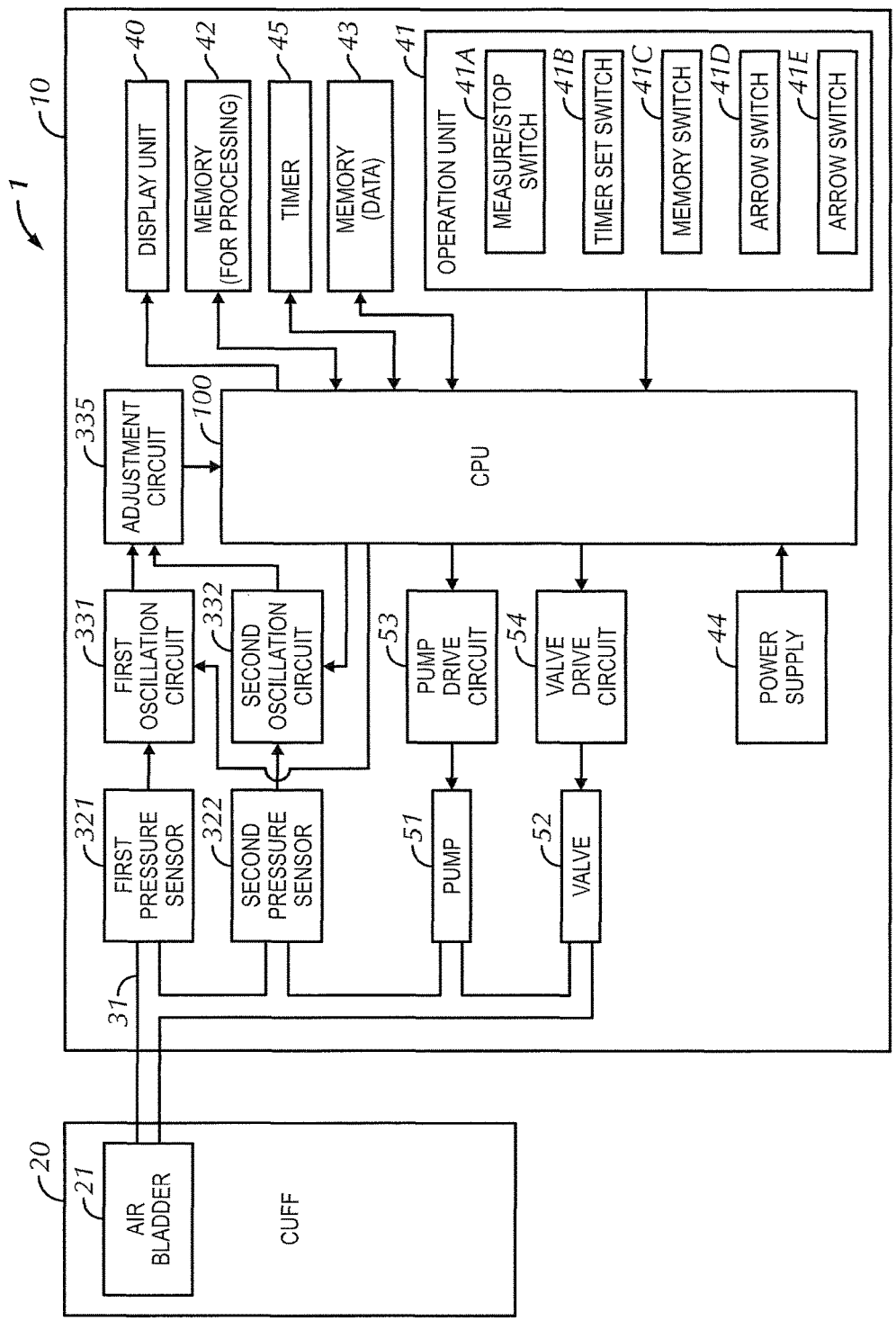
FIG. 2 is a block diagram illustrating the hardware configuration of an electronic sphygmomanometer according to an embodiment of the present invention.

FIG. 2 is a block diagram illustrating the hardware configuration of an electronic sphygmomanometer according to the embodiment of the present invention.

As seen in FIGS. 1 and 2, the electronic sphygmomanometer 1 includes a main body portion 10, a front cover 11, and a cuff 20 that can be wrapped around the upper arm of a measurement subject. The cuff 20 includes an air bladder 21. A display unit 40 configured with a liquid-crystal display or the like and an operation unit 41 configured with multiple switches for accepting instructions from a user (measurement subject) are disposed on the front cover 11.

In addition to the aforementioned display unit 40 and operation unit 41, the main body portion 10 includes: a CPU (central processing unit) 100 for carrying out centralized control of the respective elements and performing various types of computational processes; a processing memory 42 that stores programs, data, and so on for causing the CPU 100 to perform predetermined tasks; a data storage memory 43 for storing measured blood pressure data and so on; a power supply 44 for supplying power to the various elements of the main body portion 10; and a timer 45 that measures the current time and outputs the measured time data to the CPU 100.

The operation unit 41 includes: a measure/stop switch 41A that accepts the input of an instruction for turning the power on or off and accepts an instruction for starting and stopping measurement; a timer set switch 41B manipulated in order to set the timer 45; a memory switch 41C for accepting an instruction to read out information stored in the memory 43, such as blood pressure data, from the memory 43 and display that information in the display unit 40; and arrow switches 41D and 41E for accepting instructions to raise/lower numbers when setting the timer and memory numbers when calling information from a memory.

The main body portion 10 further includes a cuff pressure adjustment mechanism having a pump 51 and an exhaust valve (called simply a "valve" hereinafter) 52. An air system configured of the pump 51, the valve 52, and a first pressure sensor 321 and second pressure sensor 322 for detecting pressures within the air bladder 21 (cuff pressures) is connected, via a cuff air tube 31, to the air bladder 21 enclosed within the cuff 20.

The main body portion 10 further includes the aforementioned air system, the cuff pressure adjustment mechanism, a first oscillation circuit 331 and second oscillation circuit 332, and an adjustment circuit 335. The cuff pressure adjustment mechanism includes a pump drive circuit 53 and a valve drive circuit 54, in addition to the pump 51 and the valve 52.

The pump 51 supplies air to the air bladder 21 in order to increase the cuff pressure. The valve 52 is opened/closed in order to discharge or inject air into the air bladder 21. The pump drive circuit 53 controls the driving of the pump 51 based on a control signal supplied from the CPU 100. The valve drive circuit 54 controls the opening/closing of the valve 52 based on a control signal supplied from the CPU 100.

Electrostatic capacitance pressure sensors, for example, are used for the first pressure sensor 321 and the second pressure sensor 322. With an electrostatic capacitance pressure sensor, a capacity value changes in accordance with a detected cuff pressure. The first oscillation circuit 331 and the second oscillation circuit 332 are respectively connected to corresponding pressure sensors, and oscillate based on the capacity values of the corresponding pressure sensors. In this example, the first oscillation circuit 331 and the second oscillation circuit 332 operate in response to instructions from the CPU 100. The CPU 100 outputs an activation signal to one of the first oscillation circuit 331 and the second oscillation circuit 332.

The one of the first oscillation circuit 331 and the second oscillation circuit 332 that has received the activation signal from the CPU 100 outputs a signal having a frequency that corresponds to the capacity value of the corresponding pressure sensor (this will be called a "frequency signal" hereinafter). The outputted frequency signal is supplied to the CPU 100 via the adjustment circuit 335.

The adjustment circuit 335 is connected to the first oscillation circuit 331 and the second oscillation circuit 332, and although this will be described in detail later, allows one of the frequency signals to pass therethrough, outputting the signal to the CPU 100.

The CPU 100 detects a pressure by converting the frequency signal inputted from the first oscillation circuit 331 or the second oscillation circuit 332 via the adjustment circuit 335 into a pressure.

Figure 3:
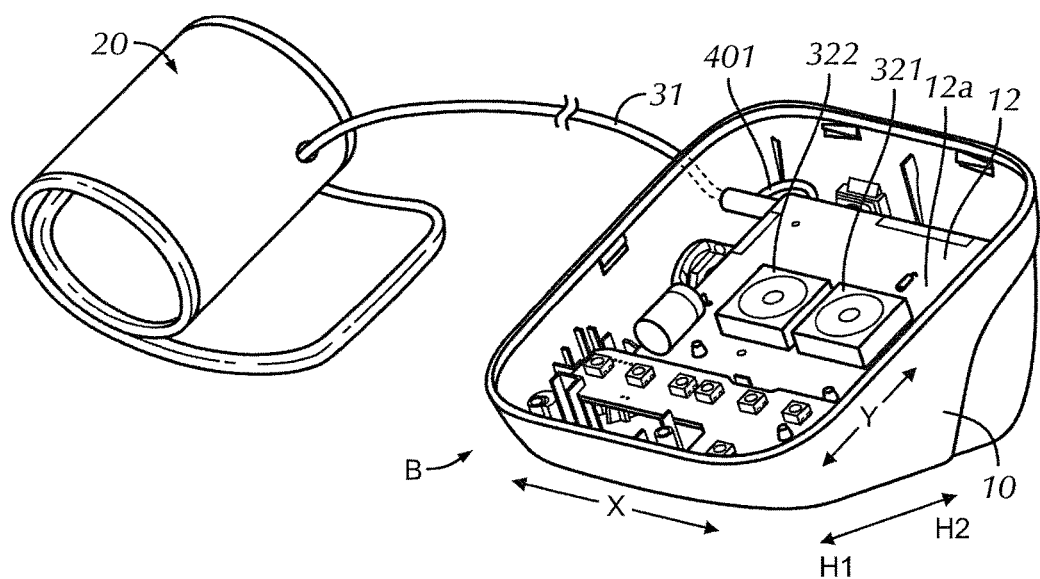
FIG. 3 is a perspective view illustrating the internal structure of the electronic sphygmomanometer 1 according to an embodiment of the present invention, where a front cover 11 has been removed from a main body portion 10.

FIG. 3 is a perspective view illustrating the internal structure of the electronic sphygmomanometer 1 according to this embodiment of the present invention, where the front cover 11 has been removed from the main body portion 10. The electronic sphygmomanometer 1 according to this embodiment has a structure in which, when the electronic sphygmomanometer 1 is placed on a mount surface B, the front cover 11 is sloped.

In order to make it easier for the user (measurement subject) to view the display unit 40 and to make it easier to operate the operation unit 41 provided in the front cover 11, the front cover 11 is sloped (the Y direction shown in FIG. 3) so that the side facing the user (measurement subject) (the front side; the side indicated as H1 in FIG. 3) is lower and the rear side (the side indicated as H2 in FIG. 3) is higher. For this reason, an internal circuit board 12 housed internally is also disposed parallel to the front cover 11, and is thus sloped so that the front side (the side indicated as H1 in FIG. 3) is lower and the rear side (the side indicated as H2 in FIG. 3) is higher.

As shown in FIG. 3, the first pressure sensor 321 and the second pressure sensor 322 are disposed on a front surface side 12a of the internal circuit board 12, which corresponds to a first main surface, along the horizontal direction (the X direction in FIG. 3) that is orthogonal to the direction in which the front cover 11 of the electronic sphygmomanometer 1 slopes.

Figure 4:
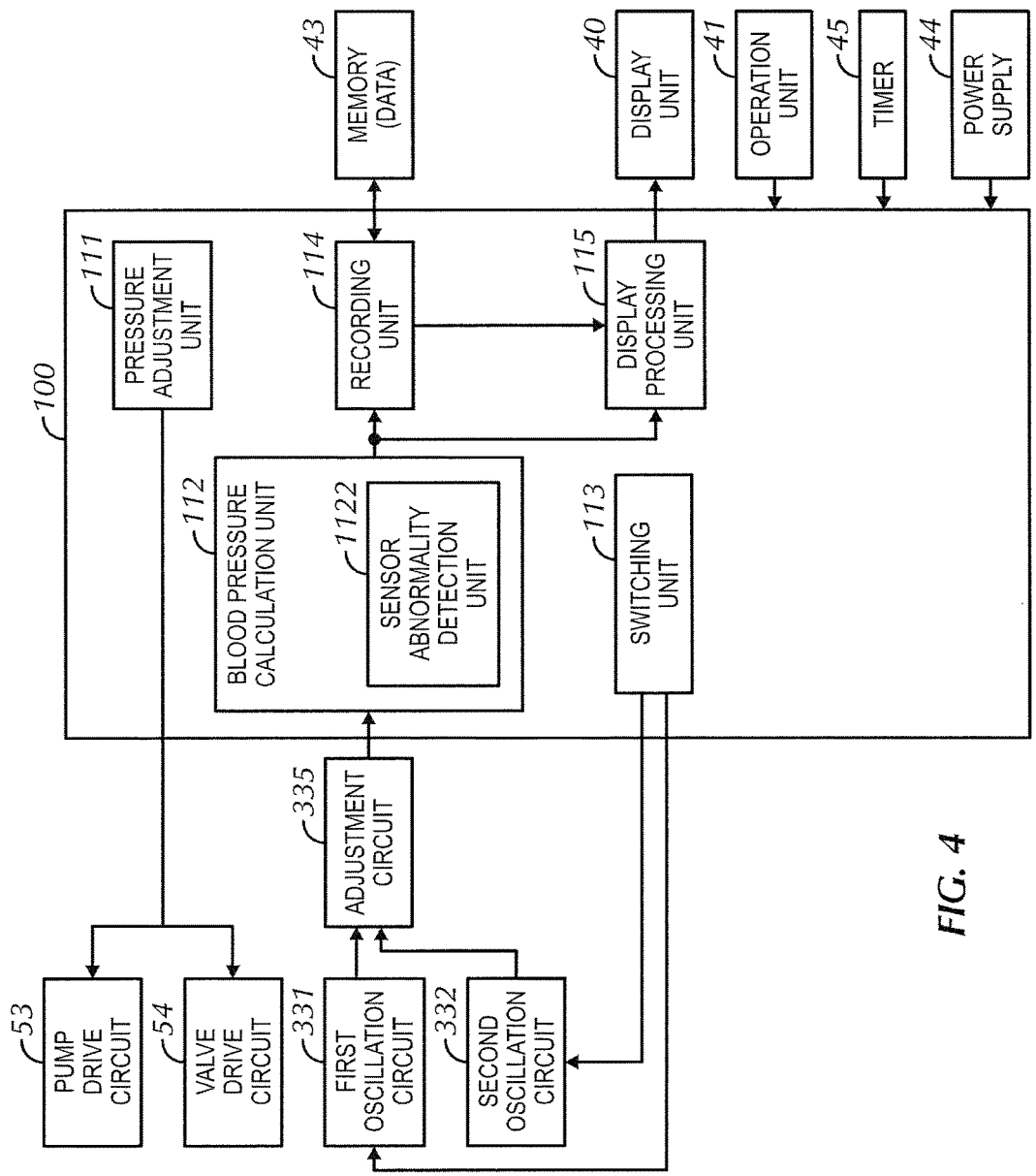
FIG. 4 is a diagram illustrating the functional configuration of the electronic sphygmomanometer 1 according to an embodiment of the present invention.

FIG. 4 is a diagram illustrating the functional configuration of the electronic sphygmomanometer 1 according to this embodiment of the present invention.

As shown in FIG. 4, the CPU 100 includes a pressure adjustment unit 111, a blood pressure calculation unit 112, a switching unit 113, a recording unit 114, and a display processing unit 115.

The pressure adjustment unit 111 adjusts the cuff pressure by controlling the pump 51 and the valve 52 via the pump drive circuit 53 and the valve drive circuit 54 in order to inject/discharge air into/from the air bladder 21 via the cuff air tube 31.

The blood pressure calculation unit 112 detects pulse wave amplitude information based on the frequency signal inputted from the first oscillation circuit 331 or the second oscillation circuit 332, calculates a systolic blood pressure and a diastolic blood pressure based on the detected pulse wave amplitude information through the oscillometric method, and also calculates the number of pulse beats per predetermined amount of time based on the detected pulse wave amplitude information. Although details will be given later, a sensor abnormality detection unit 1122 detects abnormalities in the pressure sensors.

Specifically, as the cuff pressure is gradually increased (or decreased) to a predetermined value by the pressure adjustment unit 111, the pulse wave amplitude information is detected based on the frequency signal inputted from the first oscillation circuit 331 or the second oscillation circuit 332, and the systolic blood pressure and the diastolic blood pressure of the measurement subject are calculated based on the detected pulse wave amplitude information. A known conventional method can be applied in the calculation of the blood pressure and the calculation of the pulse by the blood pressure calculation unit 112 through the oscillometric method.

The switching unit 113 switches between driving the first oscillation circuit 331 and the second oscillation circuit 332.

The recording unit 114 has functionality for reading out data from the memory 43 or writing data into the memory 43. Specifically, the recording unit 114 inputs data outputted from the blood pressure calculation unit 112, and stores the inputted data (blood pressure measurement data) in a predetermined storage region of the memory 43. In addition, the recording unit 114 reads out measurement data from a predetermined storage region of the memory 43 based on an operation made through the memory switch 41C of the operation unit 41, and outputs the measurement data to the display processing unit 115.

The display processing unit 115 inputs supplied data, converts the data into a displayable format, and displays the converted data in the display unit 40.

Figure 5A:
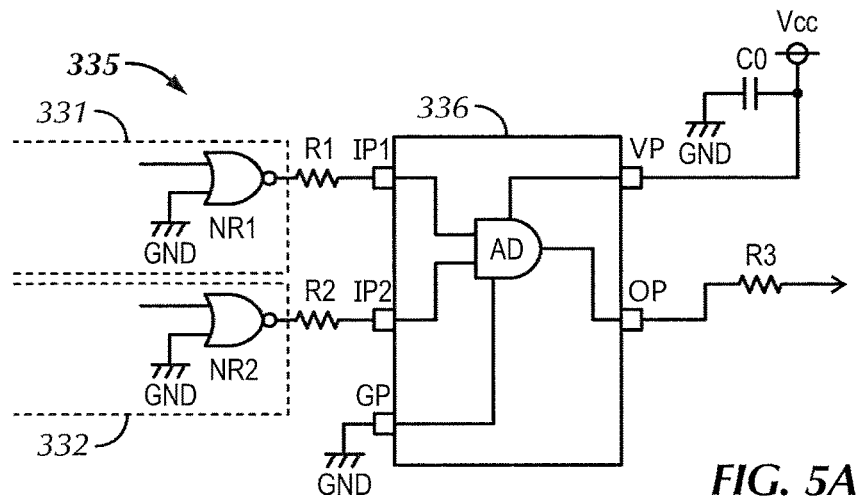
FIG. 5A is a diagram illustrating the circuit structure of an adjustment circuit 335 according to an embodiment of the present invention.
Figure 5B:
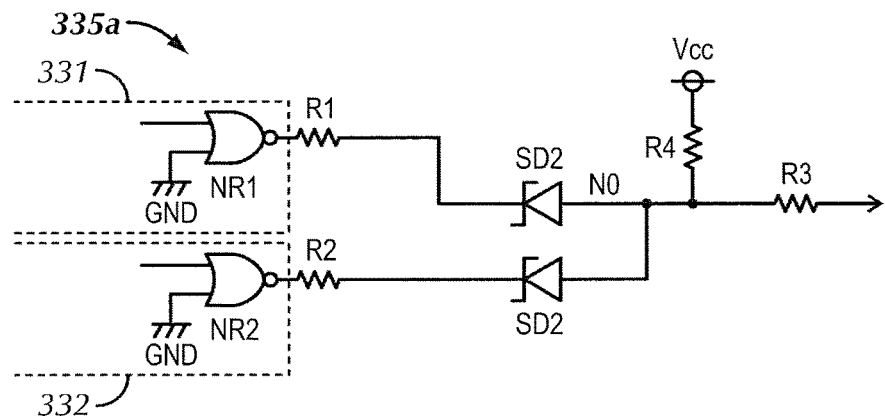
FIG. 5B is another diagram illustrating the circuit structure of the adjustment circuit 335 according to an embodiment of the present invention.
Figure 5C:
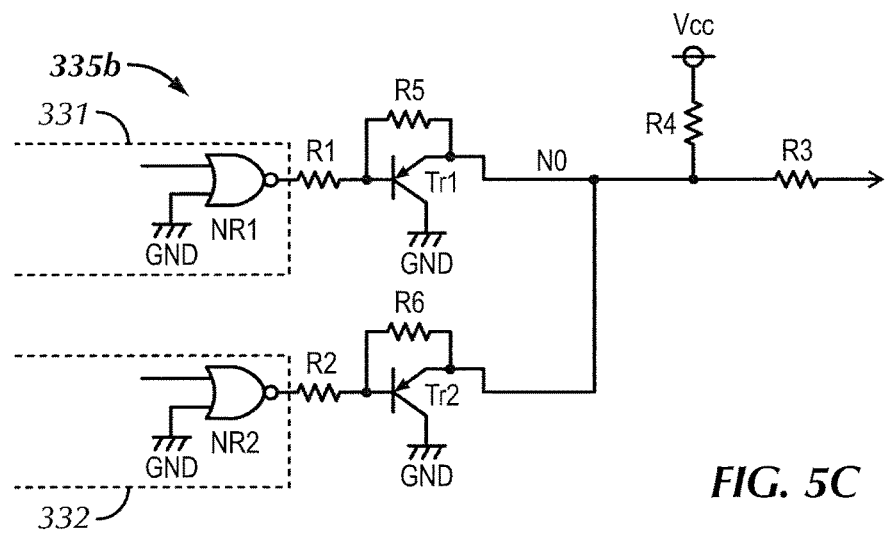
FIG. 5C is yet another diagram illustrating the circuit structure of the adjustment circuit 335 according to an embodiment of the present invention.

FIGS. 5A through 5C are diagrams illustrating circuit structures of the adjustment circuit 335 according to this embodiment of the present invention.

As shown in FIG. 5A, the adjustment circuit 335 according to this embodiment of the present invention includes an AND gate IC 336 and damping resistors R1 through R3 for adjusting the transmission properties and so on of a signal.

The AND gate IC 336 includes input terminals IP1 and IP2, power supply terminals VP and GP, and an output terminal OP. The input terminal IP1 is connected to the first oscillation circuit 331 via the damping resistor R1. The input terminal IP2 is connected to the second oscillation circuit 332 via the damping resistor R2. The power supply terminal VP is connected to a power supply voltage Vcc, whereas the power supply terminal GP is connected to a ground voltage GND. Note that a power supply capacitor C0 is also provided on the power supply terminal VP side.

Here, for example, it is assumed that the first oscillation circuit 331 is activated and a square wave frequency signal from a NOR circuit NR1 in the final stage of the first oscillation circuit 331 is inputted into the input terminal IP1 of the AND gate IC 336.

Meanwhile, the second oscillation circuit 332 is not activated, and thus, it is assumed that an output signal from a NOR circuit NR2 in the final stage of the second oscillation circuit 332 is at H level. Accordingly, it is assumed that a fixed voltage signal (in this example, an H level signal) is inputted into the input terminal IP2 of the AND gate IC 336. Such being the case, because the square wave frequency signal is inputted into the input terminal IP1 of the AND gate IC 336 and the H level fixed voltage signal is inputted into the input terminal IP2, a square wave frequency signal dependent on the input terminal IP1 is outputted from the output terminal OP as a result of an AND logic operation.

The CPU 100 receives the output signal.

Although this example describes a case in which the first oscillation circuit 331 is activated and the second oscillation circuit 332 is inactive, it should be noted that equivalent operations are performed when the scenario is reversed.

Furthermore, although this example describes an AND gate IC that uses an AND gate, an OR gate, for example, can be employed as the logic circuit, rather than an AND gate. In such a case, it is assumed, for example, that because the oscillation circuit is inactive, the output signal thereof is L level. Furthermore, the logic gate is not limited to an AND gate or an OR gate; it is of course possible to use another logic gate in accordance with the logic structure.

FIG. 5B illustrates the circuit structure of an adjustment circuit 335a.

As shown in FIG. 5B, the adjustment circuit 335a includes Schottky diodes SD1 and SD2, the damping resistors R1 through R3 for adjusting the transmission properties and so on of signals, and a pull-up resistor R4. The pull-up resistor R4 is connected between the power supply voltage Vcc and a node N0.

The Schottky diode SD1 is connected on its anode side to the node N0 and is connected on its cathode side to the NOR circuit NR1 in the final stage of the first oscillation circuit 331 via the damping resistor R1. The Schottky diode SD2 is connected on its anode side to the node N0 and is connected on its cathode side to the NOR circuit NR2 in the final stage of the second oscillation circuit 332 via the damping resistor R2.

Here, for example, it is assumed that the first oscillation circuit 331 is activated and a square wave frequency signal from the NOR circuit NR1 in the final stage of the first oscillation circuit 331 is inputted. Meanwhile, the second oscillation circuit 332 is not activated, and thus, it is assumed that an output signal from the NOR circuit NR2 in the final stage of the second oscillation circuit 332 is at H level. In this case, the node N0 is, in its initial state, set to H level in accordance with the pull-up resistor R4, but is drawn toward the ground voltage GND when the square wave frequency signal from the NOR circuit NR1 in the final stage of the first oscillation circuit 331 goes to L level; as a result, a square wave frequency signal dependent on the signal outputted from the first oscillation circuit 331 is outputted.

The CPU 100 receives the output signal.

Although this example describes a case in which the first oscillation circuit 331 is activated and the second oscillation circuit 332 is inactive, it should be noted that equivalent operations are performed when the scenario is reversed.

FIG. 5C illustrates the circuit structure of an adjustment circuit 335b.

As shown in FIG. 5C, the adjustment circuit 335b includes bipolar transistors Tr1 and Tr2, the damping resistors R1 through R3 for adjusting the transmission properties and so on of signals, the pull-up resistor R4, and bias resistors R5 and R6. The pull-up resistor R4 is connected between the power supply voltage Vcc and the node N0.

The PNP-type bipolar transistor Tr1 has its emitter connected to the node N0, its collector connected to the ground voltage GND, and its base connected to the NOR circuit NR1 in the final stage of the first oscillation circuit 331 via the damping resistor R1. The bias resistor R5 is connected between the base and the emitter.

The PNP-type bipolar transistor Tr2 has its emitter connected to the node N0, its collector connected to the ground voltage GND, and its base connected to the NOR circuit NR2 in the final stage of the second oscillation circuit 332 via the damping resistor R2. The bias resistor R6 is connected between the base and the emitter.

Here, for example, it is assumed that the first oscillation circuit 331 is activated and a square wave frequency signal from the NOR circuit NR1 in the final stage of the first oscillation circuit 331 is inputted. Meanwhile, the second oscillation circuit 332 is not activated, and thus it is assumed that an output signal from the NOR circuit NR2 in the final stage of the second oscillation circuit 332 is at H level. In this case, the node N0 is, in its initial state, set to H level in accordance with the pull-up resistor R4, but is drawn toward the ground voltage GND when the PNP-type bipolar transistor Tr1 turns on in accordance with the square wave frequency signal from the NOR circuit NR1 in the final stage of the first oscillation circuit 331 going to L level. As a result, a square wave frequency signal dependent on the signal outputted from the first oscillation circuit 331 is outputted.

The CPU 100 receives the output signal.

Although this example describes a case in which the first oscillation circuit 331 is activated and the second oscillation circuit 332 is inactive, it should be noted that equivalent operations are performed when the scenario is reversed.

By providing the adjustment circuit 335 as described above, the CPU 100 is inputted with the frequency signal from one of the first oscillation circuit 331 and the second oscillation circuit 332, and thus, a single analog input terminal is sufficient. Therefore, the scale of the circuit used for the CPU 100 can be reduced and the same CPU used in conventional electronic sphygmomanometers can be employed, even in the case where two pressure sensors are provided.

Furthermore, the adjustment circuit 335 is configured of, for example, an AND gate rather than a complex and expensive relay circuit or the like, and thus can be configured inexpensively.

Furthermore, rather than receiving inputs of frequency signals from the respective oscillation circuits of the two pressure sensors, the stated adjustment circuit 335 receives an input from only one of the oscillation circuits and receives an input of the fixed voltage signal from the other oscillation circuit. Thus, it is possible to avoid erroneous operations resulting from electromagnetic interference in the circuit, and it is not necessary to add a costly process of providing sufficient electromagnetic insulation on the circuit board. Moreover, because driving is carried out using only one of the oscillation circuits, the amount of power consumed is reduced, which makes it possible to extend the life of any batteries that are used. Further still, an increase in the scale of the circuit used for the CPU can be suppressed, which also makes it possible to reduce the amount of power consumed.

Figure 6:
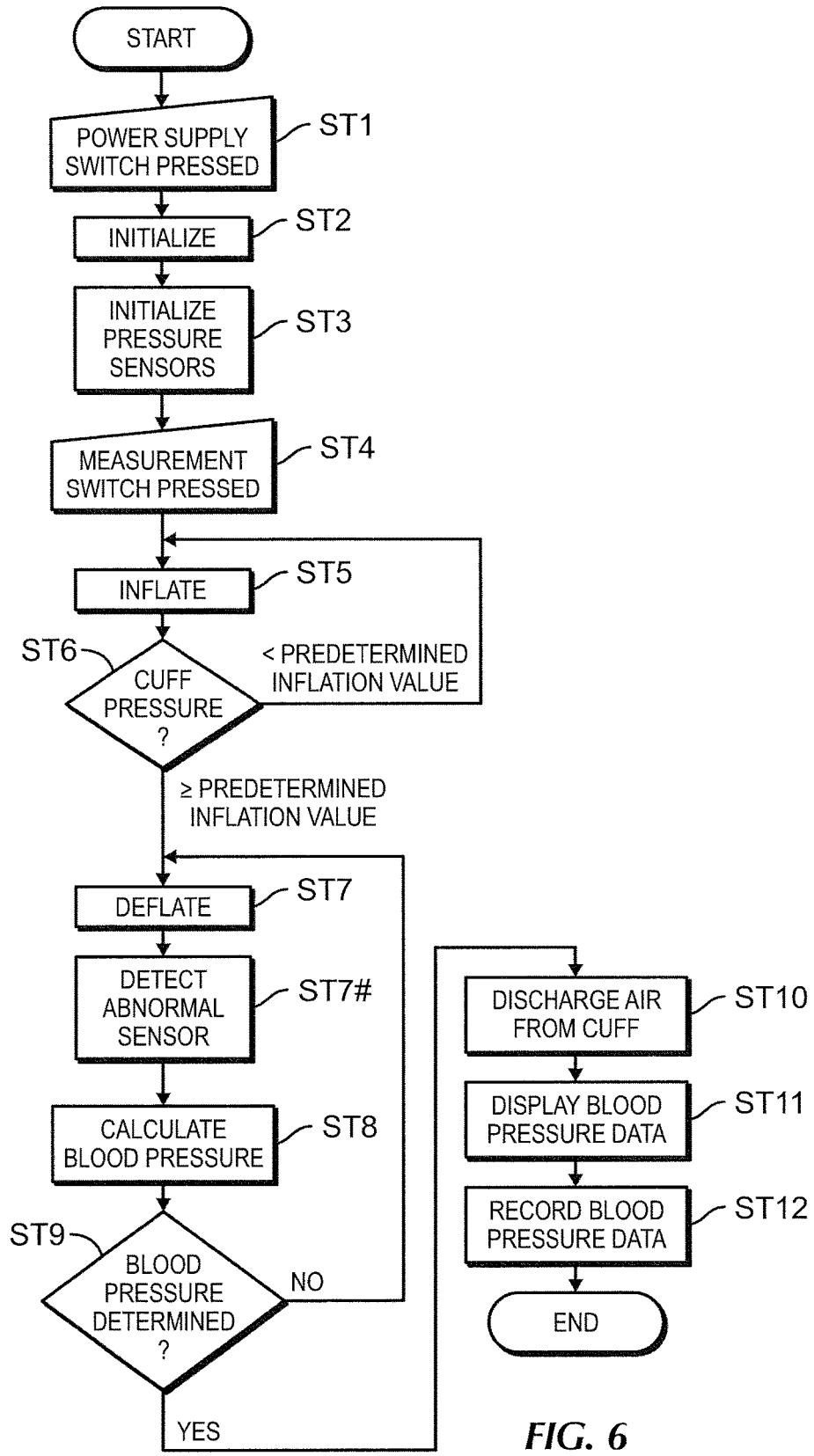
FIG. 6 is a flowchart illustrating a procedure carried out in a blood pressure measurement process according to an embodiment.

FIG. 6 is a flowchart illustrating a procedure carried out in a blood pressure measurement process according to the present embodiment.

The flowchart in FIG. 6 illustrating the stated procedure is stored in advance in a memory 42 as a program, and the blood pressure measurement process illustrated in FIG. 6 is realized by the CPU 100 reading out the program from the memory 42 and executing instructions.

First, when the measurement subject manipulates (presses) the measure/stop switch 41A (step ST1), the CPU 100 resets a working memory (not shown) (ST2).

Next, the first pressure sensor 321 and the second pressure sensor 322 are adjusted to 0 mmHg (ST3).

Here, the measurement subject wraps the cuff 20 around the measurement area and wears the cuff 20 as shown in FIG. 1. When the measurement subject operates (presses) the measure/stop switch 41A after wrapping the cuff 20 around the measurement area (step ST4), the pressure adjustment unit 111 outputs control signals to the pump drive circuit 53 and the valve drive circuit 54. Meanwhile, the switching unit 113 outputs an activation signal to the first oscillation circuit 331. However, an activation signal is not outputted to the second oscillation circuit 332. Based on the control signals, the valve drive circuit 54 closes the valve 52, and the pump drive circuit 53 drive the pump 51. As a result, the cuff pressure is gradually increased to a predetermined pressure (steps ST5, ST6). Meanwhile, in response to the activation signal, the first oscillation circuit 331 outputs a frequency signal based on the change in the capacity value of the first pressure sensor in accordance with the cuff pressure. On the other hand, the second oscillation circuit 332 is not activated, and thus the output thereof is, as mentioned earlier, fixed to a predetermined voltage signal (H level, for example). Accordingly, the frequency signal from the first oscillation circuit 331 is inputted into the blood pressure calculation unit 112, as described earlier.

Next, after the cuff 20 has been inflated to the predetermined pressure ("≥predetermined inflation value" in step ST6), the pressure adjustment unit 111 outputs control signals to the pump drive circuit 53 and the valve drive circuit 54. Based on the control signals, the pump drive circuit 53 stops the pump 51, after which the valve drive circuit 54 gradually controls the valve 52 so as to open. The cuff pressure is gradually reduced as a result (step ST7).

In the present example, an abnormal sensor detection process, for example, is executed at the beginning of this pressure reduction process (step ST7#). This abnormal sensor detection process will be described later.

Furthermore, during this pressure reduction process, the blood pressure calculation unit 112 obtains a cuff pressure signal detected by the first pressure sensor 321 based on the frequency signal outputted from the first oscillation circuit 331, and the pulse wave amplitude information is detected based on this cuff pressure signal. A predetermined computation is then carried out based on the detected pulse wave amplitude information. The systolic blood pressure and the diastolic blood pressure are calculated through this computation (steps ST8, ST9). The pulse wave amplitude information expresses a component of the change in volume of an artery in the measurement area, and is included in the detected cuff pressure signal. Note that the blood pressure measurement is not limited to being carried out during the pressure reduction process, and may instead be carried out during the process of increasing the pressure (step ST5).

When the systolic blood pressure and diastolic blood pressure have been calculated and determined (YES in step ST9), the pressure adjustment unit 111 fully opens the valve 52 via the valve drive circuit 54, and quickly discharges the air within the cuff 20 (step ST10).

The blood pressure data calculated by the blood pressure calculation unit 112 is outputted to the display processing unit 115 and the recording unit 114. The display processing unit 115 takes the blood pressure data as its input, and displays that data in the display unit 40 (step ST11). Meanwhile, the recording unit 114 takes the blood pressure data as its input, and stores that data in a predetermined storage region of the memory 43 in association with time data inputted from the timer 45 (step ST12).

Note that the blood pressure calculation unit 112 can also calculate the number of pulse beats based on the detected pulse wave amplitude information. The calculated number of pulse beats is displayed in the display unit 40 by the display processing unit 115, and is stored in the memory 43 in association with the blood pressure data by the recording unit 114.

Figure 7:
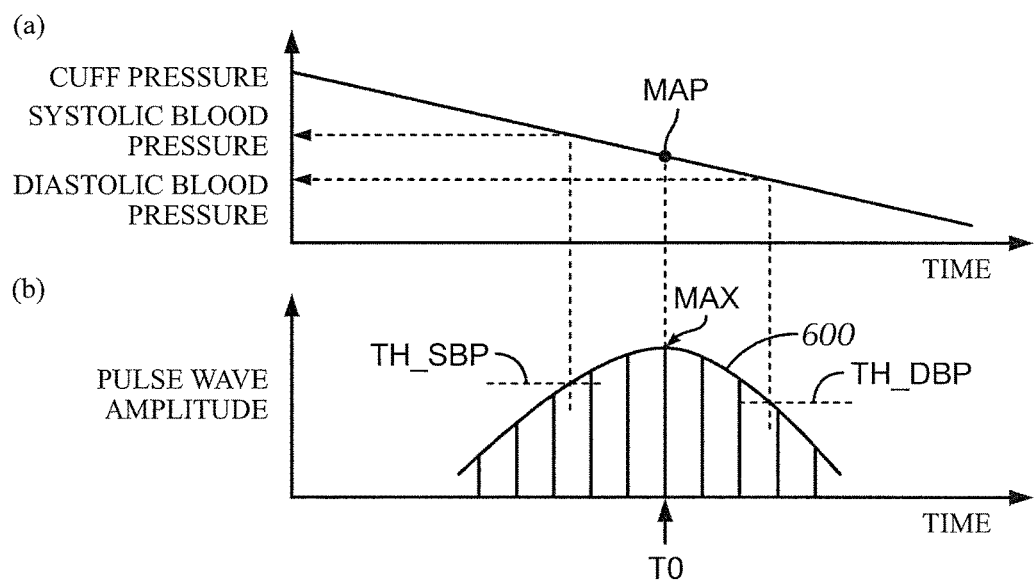
FIG. 7 is a diagram conceptually illustrating a blood pressure calculation method that uses an oscillometric method according to an embodiment of the present invention.

FIG. 7 is a diagram conceptually illustrating a blood pressure calculation method that uses an oscillometric method according to an embodiment of the present invention.

In (a) of FIG. 7, the gradually decreasing cuff pressure is illustrated along an axis of time that is measured by the timer 45. Meanwhile, (b) of FIG. 7 shows an envelope line 600 indicating a pulse wave amplitude corresponding to the stated pulse wave amplitude information, along the same time axis. The envelope line 600 indicating the pulse wave amplitude is detected by extracting, in time series, a pulse wave amplitude signal that overlaps with the signal from the pressure sensor (that is, the cuff pressure).

As shown in (a) and (b) of FIG. 7, when a maximum value MAX for the amplitude is detected in the envelope line 600 indicating the pulse wave amplitude, the blood pressure calculation unit 112 calculates two threshold values TH_DBP and TH_SBP by multiplying the maximum value by predetermined constants (for example, 0.7 and 0.5). The cuff pressure at the point where the threshold value TH_DBP and the envelope line 600 intersect on the side of the envelope line 600 where the cuff pressure is lower than a cuff pressure MAP (average blood pressure) corresponding to a point in time T0 where the maximum value MAX has been detected is taken as the diastolic blood pressure. Likewise, the cuff pressure at the point where the threshold value TH_SBP and the envelope line 600 intersect on the side of the envelope line 600 where the cuff pressure is higher than the cuff pressure MAP is taken as the systolic blood pressure.

Although the present example describes the oscillometric method, the method is not limited thereto, and another method can be employed as long as that method calculates a systolic blood pressure SBP and a diastolic blood pressure DBP by extracting pulse wave amplitude information.

Determination of Sensor Abnormalities

With conventional electronic sphygmomanometers, users have been unable to determine whether the pressure sensors, which are of utmost importance when calculating blood pressures, are operating normally or have malfunctioned. Thus, for example, in the case where a blood pressure measurement value differs greatly (for example, a difference of more than 10 mmHg) from a normal value (for example, a measurement value obtained the previous day, a measurement value obtained at a hospital, or the like), it is not known whether that value comes from actual biological information of the measurement subject or if the pressure sensor has merely malfunctioned, which has caused concern on the part of the user.

Accordingly, the electronic sphygmomanometer 1 according to the present embodiment is provided with the two pressure sensors 321 and 322, and a determination as to whether or not a sensor abnormality has occurred is carried out based on cuff pressure values detected by these pressure sensors. As a result, even in the case where one of the pressure sensors has malfunctioned due to changes over time, it is possible to determine whether an abnormality has occurred using the other pressure sensor, which in turn makes it possible to improve the reliability of blood pressure measurement values.

Figure 8:
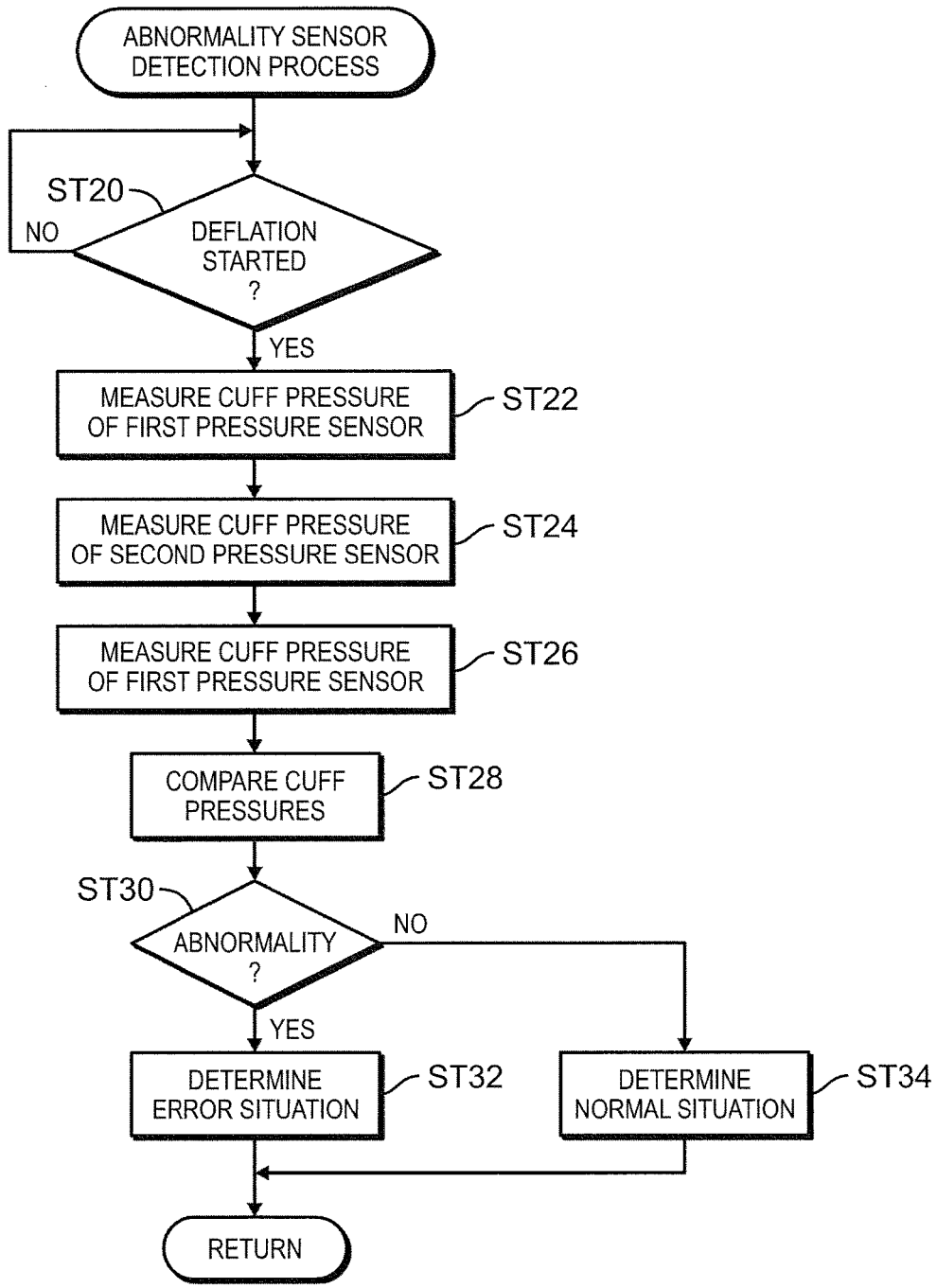
FIG. 8 is a flowchart illustrating an abnormal sensor detection process according to an embodiment of the present invention.

FIG. 8 is a flowchart illustrating an abnormal sensor detection process according to an embodiment of the present invention.

The flowchart in FIG. 8 illustrating the stated procedure is stored in advance in the memory 42 as a program, and the abnormal sensor detection process illustrated in FIG. 8 is realized by the sensor abnormality detection unit 1122, as a result of the CPU 100 reading out the program from the memory 42 and executing instructions.

Figure 9:
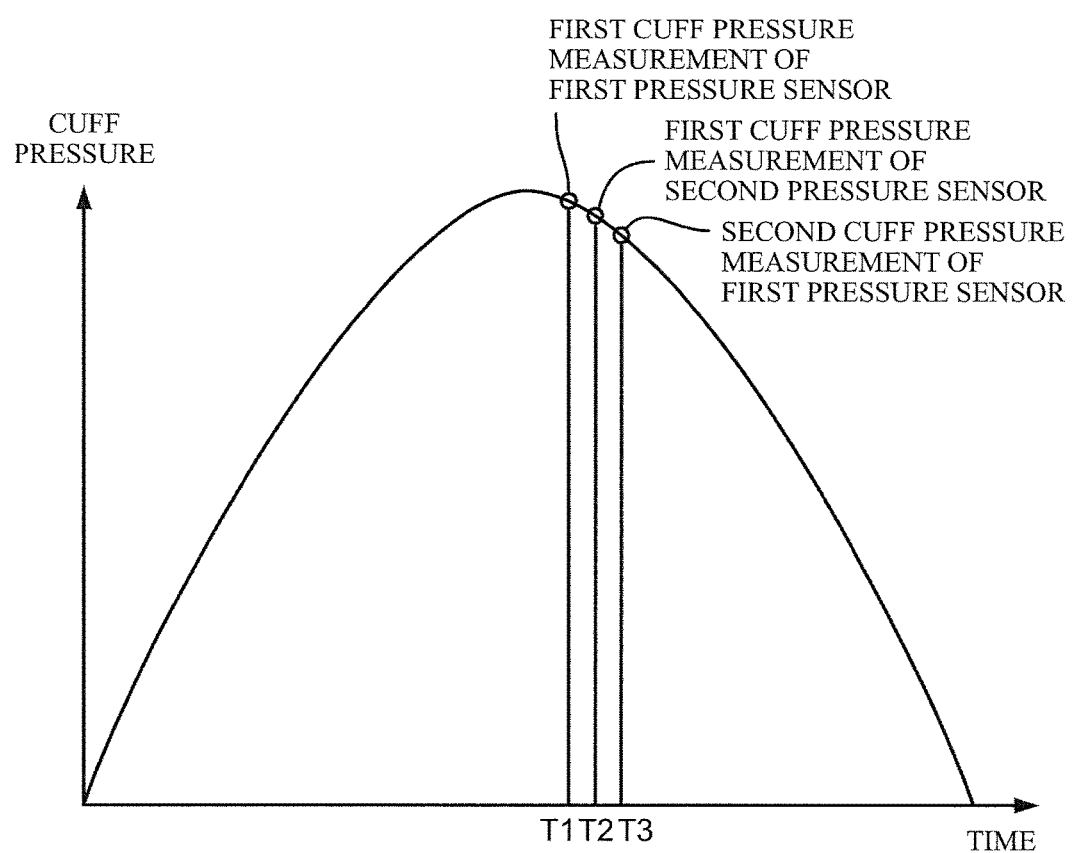
FIG. 9 is a diagram illustrating a cuff pressure measurement performed during the abnormal sensor detection process according to an embodiment of the present invention.

FIG. 9 is a diagram illustrating a cuff pressure measurement performed during the abnormal sensor detection process according to this embodiment of the present invention.

As shown in FIGS. 8 and 9, first, the CPU 100 determines whether or not deflation has started (step ST20). The state in step ST20 is maintained until the deflation has started.

Next, in the case where the deflation has started (YES in step ST20), the cuff pressure of the first pressure sensor 321 is measured (step ST22). Specifically, the cuff pressure is measured based on the frequency signal inputted from the first oscillation circuit 331 that has already been activated (a first cuff pressure measurement). In FIG. 9, a time T1 indicates the first cuff pressure measurement of the first pressure sensor 321.

Next, the cuff pressure of the second pressure sensor 322 is measured (step ST24). Specifically, the switching unit 113 of the CPU 100 outputs, to the second oscillation circuit 332, the activation signal that was being outputted to the first oscillation circuit 331. As a result, in response to the activation signal, the second oscillation circuit 332 outputs a frequency signal based on the change in the capacity value of the second pressure sensor 322 in accordance with the cuff pressure. On the other hand, the first oscillation circuit 331 is not activated, and thus the output thereof is, as mentioned earlier, fixed to a predetermined voltage signal (H level, for example). Accordingly, in this case, the adjustment circuit 335 allows the frequency signal from the second oscillation circuit 332 to pass. The frequency signal from the second oscillation circuit 332 is inputted into the CPU 100, and the cuff pressure is measured based on the inputted frequency signal. In FIG. 9, a time T2 indicates the first cuff pressure measurement of the second pressure sensor 322.

Next, the cuff pressure of the first pressure sensor 321 is measured (step ST26). Specifically, the switching unit 113 of the CPU 100 again outputs, to the first oscillation circuit 331, the activation signal that was being outputted to the second oscillation circuit 332. As a result, in response to the activation signal, the first oscillation circuit 331 outputs a frequency signal based on the change in the capacity value of the first pressure sensor 321 in accordance with the cuff pressure. On the other hand, the second oscillation circuit 332 is not activated, and thus the output thereof is, as mentioned earlier, fixed to a predetermined voltage signal (H level, for example). Accordingly, in this case, the adjustment circuit 335 allows the frequency signal from the first oscillation circuit 331 to pass. The frequency signal from the first oscillation circuit 331 is inputted into the CPU 100, and the cuff pressure is measured based on the inputted frequency signal (a second cuff pressure measurement). In FIG. 9, a time T3 indicates the second cuff pressure measurement of the first pressure sensor 321.

Next, the cuff pressures are compared (step ST28).

Specifically, the two cuff pressures detected by the first pressure sensor 321 are averaged. Then, the average of the cuff pressures detected by the first pressure sensor 321 is compared with the cuff pressure detected by the second pressure sensor 322.

As shown in FIG. 9, the cuff pressure fluctuates, and therefore the cuff pressures at the times of the detections carried out by the first pressure sensor 321 differ from the cuff pressure at the time of the detection carried out by the second pressure sensor 322. In other words, because the cuff pressure cannot be measured by the two pressure sensors at the same time, the two cuff pressures detected by the first pressure sensor 321 are averaged; that value is then assumed to be the value that would be detected by the first pressure sensor 321 at the time T2, and is compared with the cuff pressure detected by the second pressure sensor 322. Note that it is desirable for the time period in which the abnormal sensor detection process is executed to be a time in which the cuff pressure is changing linearly.

It should be noted that the example described here is merely one example. For example, the first pressure sensor 321 and the second pressure sensor 322 may be switched so that the cuff pressure of the second pressure sensor 322 is detected twice, the cuff pressure of the first pressure sensor 321 is detected once, and the cuff pressures are then compared using the same method as described above.

Alternatively, the cuff pressure may be detected once each for the first pressure sensor 321 and the second pressure sensor 322, with at least one of the cuff pressures being multiplied by a predetermined coefficient based on the different points of time of the detections and the cuff pressures then being compared; no limitations are placed on the method of the comparison.

Next, it is determined, based on the comparison, whether or not an abnormality has occurred (step ST30).

Specifically, it is determined whether or not the difference between the average of the cuff pressures detected by the first pressure sensor 321 and the cuff pressure detected by the second pressure sensor 322 has exceeded a predetermined value (for example, 5 mmHg). An abnormality is determined to have occurred in the case where the predetermined value has been exceeded. On the other hand, the situation is determined to be normal in the case where the predetermined value has not been exceeded.

In the case where it has been determined in step ST30 that an abnormality has occurred (YES in step ST30), an error is determined to have occurred (step ST32).

On the other hand, in the case where it has been determined in step ST30 than an abnormality has not occurred (NO in step ST30), it is determined that the situation is normal (step ST34).

The process then ends (return). After this, the blood pressure calculation process of step ST8 in FIG. 6 is executed as described earlier.

In the case where the sensor abnormality detection unit 1122 has determined that an abnormality has occurred in either of the pressure sensors, the blood pressure calculation unit 112 does not use the calculated blood pressure measurement data in the display/recording, or in other words, discards the data based on that determination result. This makes it possible to improve the reliability of the blood pressure measurement value. However, rather than discarding the data, information (a message) indicating that an abnormality has occurred in the pressure sensor may be displayed in the display unit 40 along with the blood pressure measurement data. Furthermore, the blood pressure measurement data may be associated with a flag indicating that an abnormality has occurred in the pressure sensor, and that blood pressure measurement data may then be stored in the memory 43. Having confirmed this display, the measurement subject can know whether or not an abnormality has occurred in the pressure sensor, which allows the measurement subject to experience at least a temporary sense of relief even if the result of the blood pressure measurement deviates from a normal value. This also makes it possible to eliminate concern about the precision of the blood pressure measurement value.

Although this example has described executing the abnormal sensor detection process of step ST7# immediately after the cuff pressure is reduced, which corresponds to a period that does not overlap with the processes in steps ST8 and ST9 of FIG. 6 that execute the blood pressure calculation, it should be noted that the abnormality detection process may be executed during any period that does not overlap with steps ST8 and ST9, such as a period from when a blood pressure has been determined to when the air is discharged from the cuff. Alternatively, this process may be executed during the inflation of the cuff.

In this manner, by using two pressure sensors, it is possible to improve the reliability of blood pressure measurement values through a simple system.

Although this example has described a case in which two pressure sensors are used, it should be noted that the invention can also be applied in the same manner in the case where three or more pressure sensors are used.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

REFERENCE NUMERALS LIST 1 electronic sphygmomanometer
10 main body portion
11 front cover
12 internal circuit board
12a front surface side
20 cuff
21 air bladder
31 cuff air tube
40 display unit
41 operation unit
41A measure/stop switch
41B timer set switch
41C memory switch
41D, 41E arrow switch
42, 43 memory
44 power supply
45 timer
51 pump
52 valve
53 pump drive circuit
54 valve drive circuit
100 CPU (Central Processing Unit)
111 pressure adjustment unit
112 blood pressure calculation unit
113 switching unit
114 recording unit
115 display processing unit
321 first pressure sensor
322 second pressure sensor
331 first oscillation circuit
332 second oscillation circuit
335 adjustment circuit
1122 sensor abnormality detection unit

The invention claimed is:

1. An electronic sphygmomanometer comprising:
   a cuff that is worn on a measurement area;
   an inflation and deflation unit that adjusts a pressure applied to the cuff;
   a plurality of pressure sensors connected to the cuff;
   a plurality of oscillation circuits, provided in correspondence to the respective plurality of pressure sensors, that output a square wave signal of a frequency based on pressures;
   an oscillation circuit adjustment circuit having a plurality of input terminals to receive signals from the plurality of oscillation circuits, and having only one output terminal that allows the output of the square wave signal from one of the plurality of oscillation circuits to pass; and
   a CPU having only one analog input terminal that is configured to accept an input of the square wave signal from the one output terminal of the oscillation circuit adjustment circuit and configured to calculate a blood pressure from the frequency of the square wave signal,
   wherein the CPU comprises a switching unit that outputs an activation signal that is applied selectively to one of the plurality of oscillation circuits so that when one oscillation circuit is activated by the activation signal, the remaining oscillation circuits are not activated, and
   wherein the CPU is further configured to determine whether or not an abnormality has occurred in the plurality of pressure sensors, upon comparing the blood pressures obtained from the plurality of oscillation circuits associated with the plurality of pressure sensors, respectively.

2. The electronic sphygmomanometer according to claim 1,
   wherein the oscillation circuit adjustment circuit comprises a logic circuit, comprising a plurality of input nodes that accept signals input from the respective plurality of oscillation circuits, that outputs one signal based on a result of a logic process performed on the signals inputted into the plurality of input nodes.

3. The electronic sphygmomanometer according to claim 2,
   wherein each of the oscillation circuits outputs a square wave signal of a frequency based on the pressure when the oscillation circuit has been activated in accordance with an instruction, and outputs a fixed voltage signal when the oscillation circuit has not been activated.

4. The electronic sphygmomanometer according to claim 1,
   wherein the CPU is configured to output a first activation signal to a first oscillation circuit among the plurality of oscillation circuits and detects a first cuff pressure based on a frequency of a first square wave signal outputted from the first oscillation circuit,
   wherein the CPU is configured to output a second activation signal to a second oscillation circuit among the plurality of oscillation circuits and detects a second cuff pressure based on a frequency of a second square wave signal outputted from the second oscillation circuit, and
   wherein the CPU is configured to determine whether or not an abnormality has occurred in the plurality of pressure sensors based on a difference between the first cuff pressure and the second cuff pressure.

5. The electronic sphygmomanometer according to claim 4,
   wherein the controller CPU is configured to output a third activation signal to the first oscillation circuit among the plurality of oscillation circuits after outputting the first activation signal and the second activation signal, and detects a third cuff pressure based on the frequency of the first square wave signal outputted from the first oscillation circuit, and
   wherein the CPU is configured to determine whether or not an abnormality has occurred in the plurality of pressure sensors based on a difference between an average of the first and third cuff pressures and the second cuff pressure.

* * * * *